United States Patent
Zhou et al.

(10) Patent No.: US 12,220,539 B2
(45) Date of Patent: Feb. 11, 2025

(54) ANTI-INFECTION FLUIDIC CHANNEL

(71) Applicant: CALIFORNIA INSTITUTE OF TECHNOLOGY, Pasadena, CA (US)

(72) Inventors: Tingtao Zhou, Los Angeles, CA (US); Xuan Wan, Pasadena, CA (US); Paul W. Sternberg, San Marino, CA (US); Chiara Daraio, South Pasadena, CA (US); Zhengyu Huang, Beijing (CN); Zongyi Li, Alhambra, CA (US); Zhiwei Peng, Mississauga (CA); John F. Brady, Pasadena, CA (US); Animashree Anandkumar, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 18/896,646

(22) Filed: Sep. 25, 2024

(65) Prior Publication Data

US 2025/0018148 A1 Jan. 16, 2025

Related U.S. Application Data

(63) Continuation of application No. 18/604,162, filed on Mar. 13, 2024, now Pat. No. 12,128,189.

(60) Provisional application No. 63/451,788, filed on Mar. 13, 2023, provisional application No. 63/602,756, (Continued)

(51) Int. Cl.
*A61M 25/00* (2006.01)

(52) U.S. Cl.
CPC ... *A61M 25/0017* (2013.01); *A61M 2025/006* (2013.01)

(58) Field of Classification Search
CPC ........ A61M 25/0017; A61M 2025/006; A61M 25/0023; A61M 2025/0056; A61M 2025/0058; A61M 2210/1089; A61M 25/00; A61M 25/0045; A61M 27/008; A61M 2025/0019; A61M 2205/0205; B08B 17/065; B08B 17/06; Y02T 50/10; Y02T 70/10; Y02T 50/60; B82Y 30/00; B82Y 10/00; B82Y 40/00; F15D 1/12; F15D 1/0035; F15D 1/004
See application file for complete search history.

(56) References Cited

U.S. PATENT DOCUMENTS

| | | | |
|---|---|---|---|
| 12,128,189 B2 | 10/2024 | Zhou et al. | |
| 2013/0125992 A1* | 5/2013 | Krautschick | F15D 1/065 264/293 |

(Continued)

OTHER PUBLICATIONS

Certification Statement and list—37 CFR 1.98(d)(1) filed in Continuation filed on Sep. 25, 2024, of U.S. Appl. No. 18/604,162, on behalf of California Institute of Technology, 1 page. Created Sep. 25, 2024.

*Primary Examiner* — Adam Marcetich
(74) *Attorney, Agent, or Firm* — Steinfl + Bruno LLP

(57) ABSTRACT

Systems and methods for altering the geometry of a fluid channel to prevent upstream mobility of bacteria, using angled obstacles on the interior of the channel that among other things creates vortices that restrict the mobility. An optimized geometry can be realized by an artificial intelligence algorithm or similar methods based on performance of various configurations of obstacle parameters.

7 Claims, 20 Drawing Sheets

Related U.S. Application Data filed on Nov. 27, 2023, provisional application No. 63/554,052, filed on Feb. 15, 2024.

(56) References Cited

U.S. PATENT DOCUMENTS

| | | | |
|---|---|---|---|
| 2015/0377562 A1* | 12/2015 | Buckrell | B23P 15/26 |
| | | | 165/181 |
| 2017/0157653 A1* | 6/2017 | Parker | B82Y 40/00 |
| 2023/0373609 A1* | 11/2023 | Togami | F15D 1/004 |
| 2024/0307654 A1 | 9/2024 | Zhou et al. | |

\* cited by examiner

ANTI-INFECTION FLUIDIC CHANNEL

CROSS-REFERENCE TO RELATED APPLICATIONS AND PAPERS

The present application is a continuation of U.S. Non-Provisional patent application Ser. No. 18/604,162, filed on Mar. 13, 2024, for "Anti-Infection Fluidic Channel", which claims priority to U.S. Provisional Patent Application No. 63/451,788, filed on Mar. 13, 2023, U.S. Provisional Application 63/602,756, filed on Nov. 27, 2023, and U.S. Provisional Application 63/554,052, filed on Feb. 15, 2024, the disclosures of which are incorporated herein by reference in their entirety. This application may also be related to the paper "AI-aided Geometric Design of Anti-infection Catheters" by Tingtao Zhou et al., arXiv:2304.14554v1 (27 Apr. 2023) and the paper "AI-aided geometric design of anti-infection catheters" by Tingtao Zhou et al., Sci. Adv. 10, eadj1741 (2024), the disclosures of which are incorporated herein by reference in their entirety.

BACKGROUND

Bacteria can swim upstream in a narrow tube and pose a clinical threat of urinary tract infection to patients implanted with fluidic channels such as catheters, stents, or similar devices. Coatings and structured surfaces have been proposed to repel bacteria, with limited results.

SUMMARY

An improved fluidic channel geometric design has been developed that allows for the construction of an anti-infection channel that is highly effective at preventing upstream movement of bacteria.

In an aspect of the invention, an article comprising a fluidic channel designated as having a flow direction is described, the article comprising: a plurality of protuberances on an interior surface of the fluidic channel, each of the protuberances having a first side facing into the flow direction at a first angle from the interior surface and a second side facing away from the flow direction at a second angle from the interior surface and a vertex between the first side and the second side and a base length from where the first side connects to the interior surface to where the second side connects to the interior surface; the first angle being different from the second angle, such that each protuberance has an asymmetrical profile; and the base length of each of the plurality of protuberances being less than one fourth the distance between vertices of adjacent protuberances.

DETAILED DESCRIPTION

As described herein, improved channel geometry design allows for improved anti-infection in biological/medical use, and artificial intelligence modelling or similar optimization methods can be used to find an optimized version of this improved geometry.

Design Algorithm

Normally, passive particles are convected downstream in addition to diffusive spreading. However, the self-propulsion of microbes results in qualitatively different macroscopic transport: the body of a bacterium crossing the tract is rotated by fluid vorticity, which leads them to swim against the flow direction. Both biological micro-swimmers and synthetic active particles exhibit upstream motility. For biological micro-swimmers such as *E. coli* and mammalian sperm, the fore-aft body asymmetry and the resulting hydrodynamic interactions with the wall are often used to explain their upstream swimming behavior. On the other hand, for point-like active particles with negligible size, upstream swimming is still present. Consider a point-like active particle when it is approaching a wall, its forefront must point into the wall. Near the wall, the vorticity of the Poiseuille flow (at its maximum) acts to always reorient the particle towards the upstream direction, and then they swim upstream along the wall (see e.g., FIGS. 1 and 2). Many other factors such as body shape asymmetry, flagellar chirality, and hydrodynamic interactions between the bacteria and the boundary also influence the upstream swimming behaviors.

Channel Wall Geometry

The general design for resisting upstream mobility of bacteria in flow channels (e.g. catheters) consists of creating obstacles (protuberances) along the inner wall of the flow channel consisting of periodic structures that have asymmetric angular shapes that create vortices that disrupt the movement of the bacteria and trap the bacteria on the down-stream side of the obstacles.

AI-Aided Optimization of Channel Wall Geometry

AI (artificial intelligence) based models such as neural operators can be used to learn surrogates for forward simulation or observational models in fluid dynamics and other domains. Since these models are differentiable, they can be directly used for inverse design, i.e., gradients can be used to optimize in the design space directly. This makes generating novel designs much more streamlined. An AI model or other optimization methods can be used to optimize the channel shape, characterized by, for example, four parameters and two constraints.

The parameter space for design optimization in this example is characterized by four parameters: obstacle (geometric protrusion around the channel inner diameter) base length L, height h, tip position s, inter-obstacle distance d, and the channel width W (see FIG. 7D). To optimize this space, two constraints are placed.

Figure 7A:
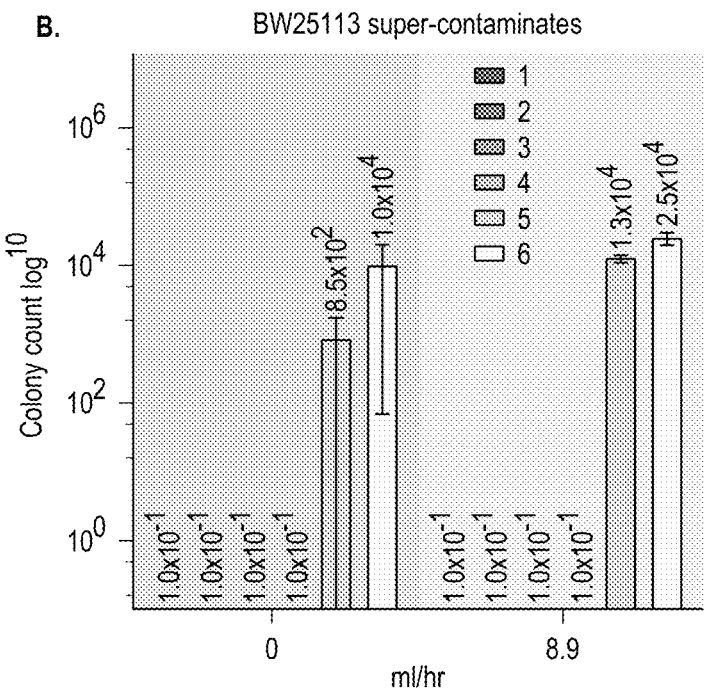
FIGS. 7A-7B show examples of results on 3D printed catheter prototypes.
Figure 7B:
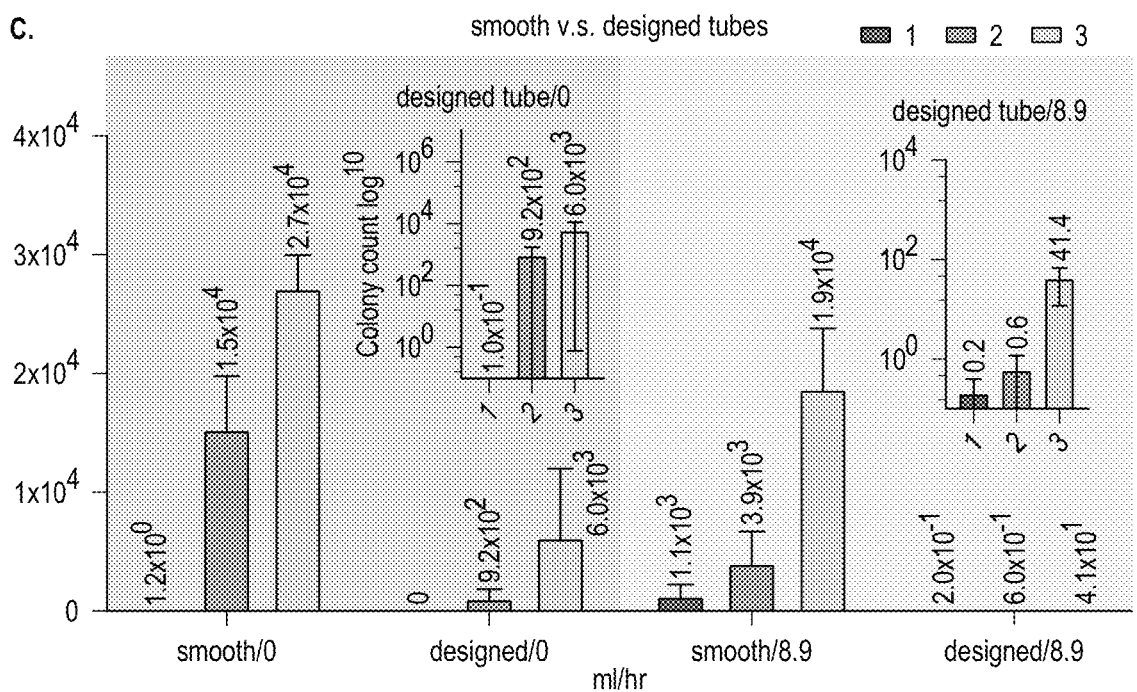

First, if neighboring obstacles get too close, the vortices at their tips start to overlap which reduces the effectiveness of the system because the vortices help disrupt the bacteria motion (see FIG. 7B). Both the magnitude of the maximum effective vorticity (right at the obstacle tips, see the mathematical definition of the effective vorticity) and the effective sizes of the vortices are reduced due to the overlap. Besides, larger boundary layer and stagnation zones develop. Hence, the inter-obstacle distance is constrained to d>0.5 W (inter obstacle distance is greater than half the channel width).

Second, with other parameters fixed, the effective vorticity at the obstacle tips increases as h increases, which is desirable to promote the vortex-redirecting effect. However, the channel tends to clog more as h increases, and would be completely blocked by the obstacles when h=W/2. This trend of stronger clogging as h increases is reflected in the continuous increase of pressure drop that is needed to maintain the same effective flow speed. To avoid clogging, constrain the height, for example to h<0.3 W.

This AI-based method first maps the irregular channel geometry to a function in the latent space (a unit segment [0,1]), then applies the FNO (Fourier Neural Operator) model in the latent space (specifically geometric FNO, or "Geo-FNO"), and finally transforms the bacteria distribution back to the physical space (see FIG. 7E). This trained surrogate model can be used for inverse design optimization, to determine the optimal channel shape (i.e., obstacle shape and spacing). To evaluate the effectiveness of each design, one can measure the averaged $\langle x_{up} \rangle$ (see below) at e.g., T=500 s for three flow speeds (e.g., 5, 10, 15 μm/s). The AI-aided shape design, based on geometry-aware Fourier neural operator, outperforms given shapes in training data by about 20% in terms of weighted bacteria distribution. The whole design optimization process is fast: about 30 minutes each to generate a training instance for a total of 1000 instances in parallel (on 50 GPUs for 10 hours), 20 minutes on 1 GPU to train the model, and 15 seconds on 1 GPU for the trained AI model to generate the optimal design. In an example, the optimization procedure leads to the optimal structure of (d=62.26, h=30.0, s=−19.56, L=15.27) μm for channel width W=100 μm. According to the mechanism presented above, this structure provides strong geometric rectification and vortex-redirecting effects to suppress upstream swimming.

The Stokes flow inside a channel can be simulated with no-slip boundary conditions using the COMSOL software. The resulting velocity and vorticity fields are then coupled into the particle dynamics simulations, while the feedback of particle motion on the fluid dynamics is neglected in the limit of dilute suspensions and small particle sizes. The particle dynamics is described by the Active Brownian Particle (ABP) model with Gaussian statistics and the run-and-tumble (RTP) model with power-law (Levy) statistics. In the ABP model, individual particle dynamics is integrated according to the over-damped Langevin equation $$0 = -\zeta(U-u) + \zeta(U_0 \eta(t) + \sqrt{2D_T}\xi(t)$$

$$dq/dt = (1/2\omega + B\ q \times (E \cdot q) + \sqrt{2/\tau_R}\eta(t)) \times q$$

where $\zeta$ is the viscous drag coefficient, U the particle's velocity, q the particle's orientation vector, u the local flow velocity, ω the local flow vorticity vector, and E the local strain-rate tensor of the flow. B is a geometric coefficient, which equals 1 for infinitely thin rods and 0 for spheres. This example uses B=0 since its value does not significantly affect the upstream swimming statistics. $\xi(t)$ is Gaussian random noise satisfying $\langle \xi(t) \rangle = 0$ and $\langle \xi(0)\xi(t) \rangle = \delta(t)I$.

As bacteria are micron-sized particles, their Brownian motion is relatively weak, and the translational diffusivity can be set to $D_T = 0.1$ μm2/s in the simulations. Varying this value does not affect the results much as long as it remains small. η is Gaussian noise with $\langle \eta(t) \rangle = 0$ and $\langle \eta(0)\eta(t) \rangle = \delta(t)I$, and $\tau_R$ is the average runtime. In the RTP model, individual particles will be displaced with η(t)=0 (the 'run' phase) for $0 < t < \tau_R$. Then q is changed instantaneously to a random new direction (the 'tumble') q' and the process repeated with a new run time $\tau_R'$.

For Levy swimmers, the runtime is sampled from Pareto distribution $\phi(\tau) = (\alpha \tau_0^\alpha)/(\tau + \tau_0)^{\alpha+1}$, where the parameter $1 < \alpha < 2$ controls the power-law index. Bacteria shape was simplified as spheres with negligible size. For the mechanism demonstration in FIG. 2J, we simulate 1,000,000 particles with a persistent run time $\tau_R = 2$ s for 200 s in a 2D channel 50 μm wide.

A periodic boundary condition for both the flow field and the particle dynamics is always imposed along the direction of the channel. As a result, the channel is effectively infinitely long, and the obstacles are, in this example, repeated every 100 μm. The particles are released at x=0 in the computational domain, initially uniformly distributed across the channel and randomly oriented. For the designed channels, sliding (for the particle dynamics) and no-slip (for the fluid dynamics) boundary conditions are imposed at the geometric boundary of the walls, except for the surface coating case where the no-slip boundary is at the wall and the sliding boundary condition for the particles are set at 3 μm away from the wall.

Geo-FNO Model and Machine Learning Setup

The catheter design problem is a Stochastic Partial Differential Equation (SPDE) constrained optimization problem, where the objective function $$\langle x_{up} \rangle = -\int_0^{-\infty} \rho(x)x\,dx \approx -\frac{1}{N}\sum_{i=1}^{N} x_i$$

depends on the SPDE solution of the fluid and particle dynamics problem. Here ρ(x) is the empirical bacteria distribution function at T=500 s, approximated by N bacteria.

Traditional optimization approaches require repeatedly evaluating such expensive computational models, and an adjoint solver is required when gradient-based optimization is applied. To overcome these computational challenges, a Geo-FNO G can be trained as a surrogate model for the forward fluid and particle dynamics simulation that maps the channel geometry to the bacteria population function G: c→ρ. In contrast, prior work using AI approaches for various design problems only chose a few parameters that are input to traditional solvers of SPDE.

The full model consists of 5 Fourier neural layers with the GeLU (Gaussian Error Linear Units) activations following and has a fast quasi-linear time complexity. Fluid and particle dynamics simulations can be performed using both the ABP (Active Brownian Particle) and Levy RTP (Run-and-Tumble Particle) models for three maximum flow speeds (e.g., 5, 10, 15 μm/s) to generate training and testing data for the Geo-FNO. For the training data, generate e.g., 1000 simulations in parallel on 50 GPUs (graphical processing units) for 10 hours, with the design in each simulation randomly selected from the following parameter space: for example, obstacles with height 20 μm<h<30 μm are periodically placed on the channel walls with inter-obstacle distance 60 μm<d<250 μm, the base length satisfies 15 μm<L<d/4, and the tip position satisfies −d/4<s<d/4. The constraints on these parameters can be chosen to satisfy fabrication limits and physical conditions for the vortex generation mechanism. The dataset can be stored to be reused for future tasks. The relative empirical mean square error can be used as the loss function. This model gets around 4% relative error on 100 testing data points.

Fast Inverse Design with Gradient-Based Optimization

The benefit of this AI approach is the speedup compared to traditional solvers, and differentiability allows the use of fast gradient-based methods for geometry design optimization. Each evaluation takes only 0.005 seconds on GPUs in contrast to 10 minutes by using GPU-based fluid and particle dynamics simulations, and therefore it is affordable to do thousands of evaluations in the optimization procedure. Moreover, this system uses automatic differentiation tools of deep learning packages to efficiently compute gradients with respect to design variables enabling the use of gradient-based design optimization methods. During optimization, start from initial design parameters (e.g., d=100, h=25, s=10, L=20) μm, and update them using the BFGS algorithm to minimize the objective function $<x_{up}>$ post-processed from the bacteria population predicted by Geo-FNO.

When the optimization gets trapped in a local minimizer, the optimization restarts from an initial condition obtained by perturbing the recorded global minimizer with a random Gaussian noise sampled from N(0,I). The randomized BFGS algorithm guarantees the recorded-global minimizer monotonically decreases. For example, the AI-based optimization took in one case approximately 1500 iterations to reach the optimal design. The entire process, from data generation (which took 30 minutes each on 1000 instances in parallel on 50 GPUs for 10 hours) to training (20 minutes on 1 GPU), design optimization (15 seconds on 1 GPU), and final verification (10 minutes on 1 GPU), took less than one day. Within imposed parameter constraints, $<x_{up}>$ is generally smaller with larger h, smaller d, and larger s. The final optimized design in this example is (d=62.26, h=30.0, s=−19.56, L=15.27) μm.

The takeaways from the geometric design process and parameter optimization showed that an improved anti-infection flow channel can be created by altering the interior walls of the channel to include obstacles that have certain general parameters: if the obstacles were of sufficient size, were sufficiently spaced apart, and were of a general triangular or trapezoid shape angled in the downstream direction, then bacteria would have greatly reduced upstream mobility.

In some embodiments, the channel is a catheter of 5 Fr to 36 Fr in outer diameter. In some embodiments, the channel width is 1 mm to 100 mm. In some embodiments, the relative values of the parameters are 50<d<70, 20<h<40, −30<s<−10, and 10<L<30. In some embodiments, a ratio (d/W) of the distance (d) between the vertex to a vertex of a neighboring protuberance to a diameter of the fluidic channel (W) is over 0.3. In some embodiments, this ratio (d/W) is over 0.5. In some embodiments, this ratio (d/W) is less than 10. In some embodiments, the vertex inter-obstacle distance (see FIGS. 8A-8D described below) is at least 60 μm. In some embodiments, the obstacle base length is no more than half the distance between the vertex and a vertex of a neighboring protuberance. In some embodiments, the obstacle base length is at least 15 μm. In some embodiments, a height of the vertex of each protuberance is at least 20 μm from a base of that protuberance, and a ratio of the height to a diameter of the fluidic channel is no more than 0.3.

Figure 1:
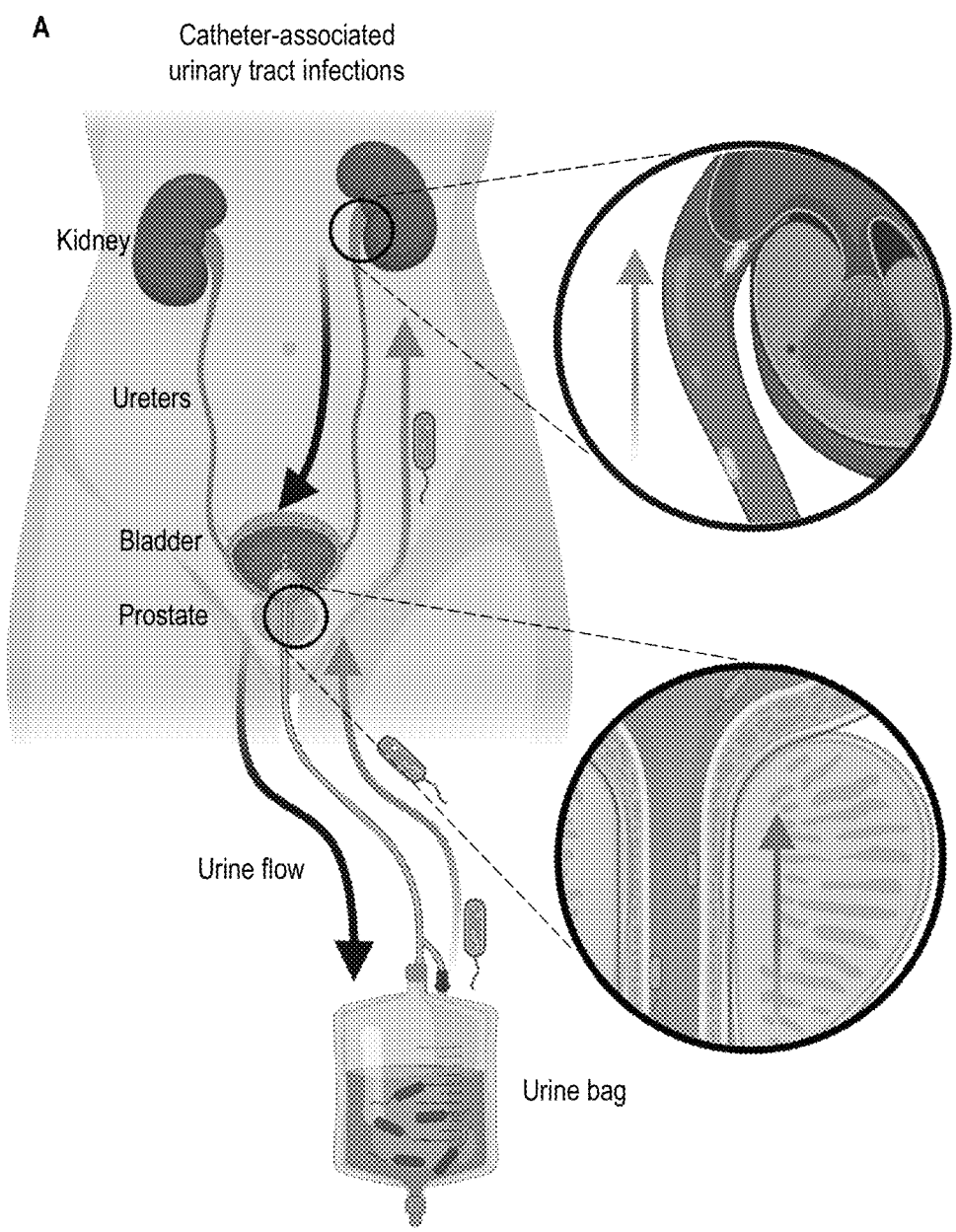
FIG. 1 shows an example use of the anti-infection geometry in a catheter.

FIG. 1 shows an example use for the anti-infection system, in this example a catheter design where the concern is urinary tract infections caused by upstream mobile bacteria from the urine bag.

Figure 2:
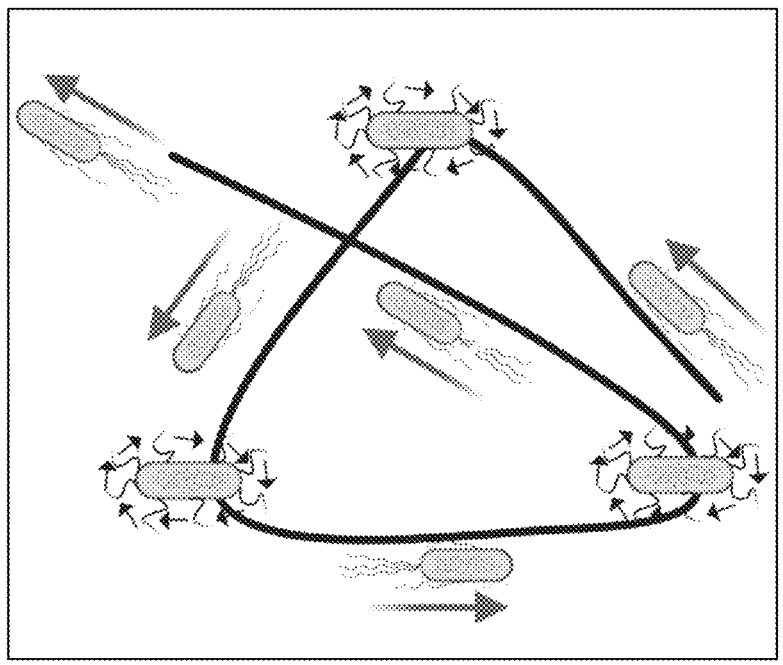
FIG. 2 shows an example diagram of run-and-tumble motion of bacteria that causes upstream mobility.
Figure 2:
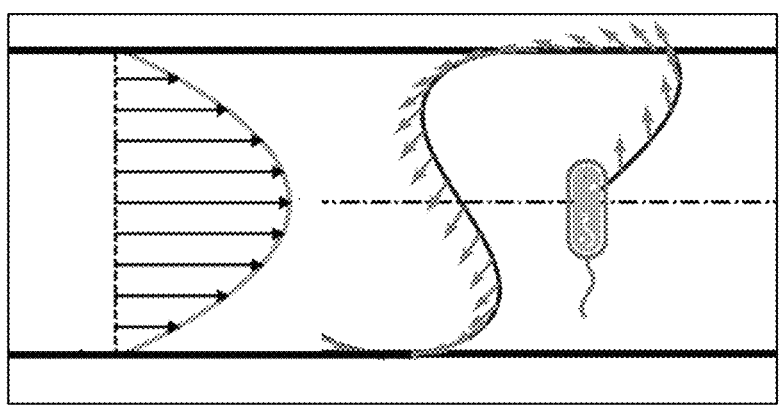

FIG. 2 shows an example of run-and-tumble motion from bacteria that causes upstream mobility.

Figure 3:
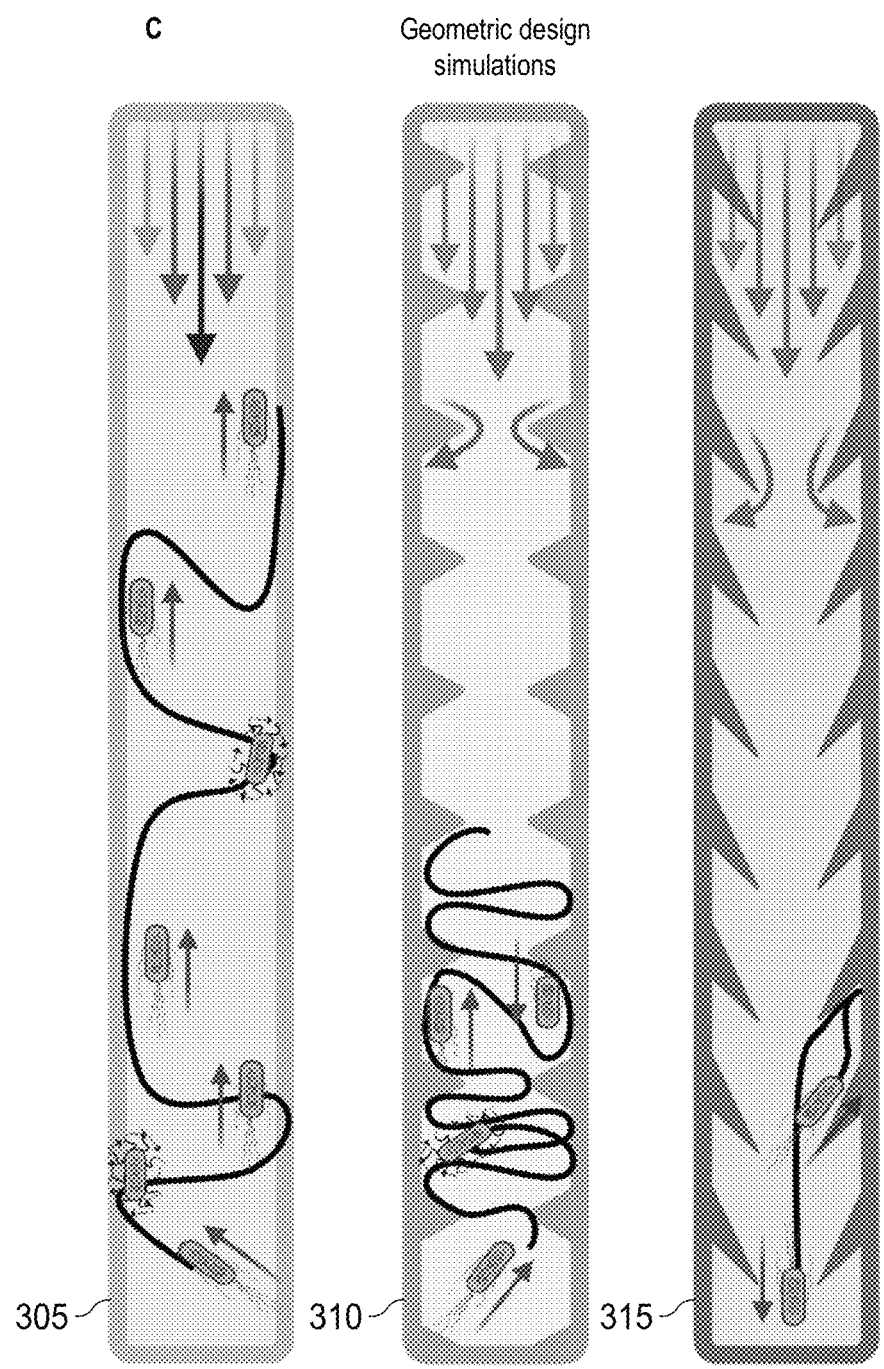
FIG. 3 shows example geometric designs for channels and the simulated mobility for each.

FIG. 3 shows three examples of channel design tests for simulation or experiment: smooth walls (305), symmetric obstacles (310), and asymmetric obstacles (315). As seen, simulations show decreased upstream mobility with obstacles (310) and even better performance with asymmetric obstacles (315) as described herein.

Figure 4:
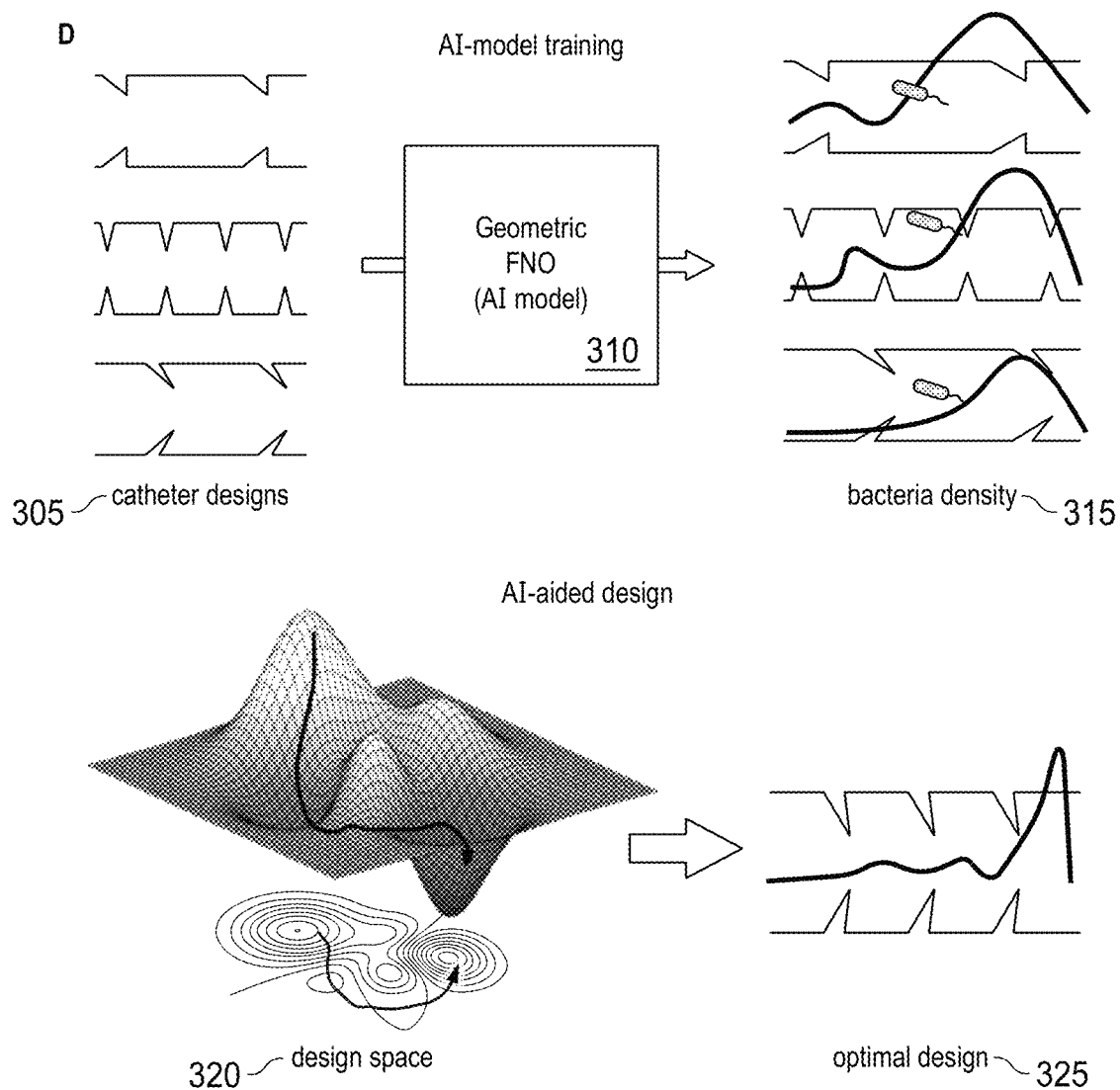
FIG. 4 shows an example diagram for using artificial intelligence modelling for optimizing anti-infection geometries.

FIG. 4 shows an example of the AI-based parameter optimization process. A series of various channel (in this example, catheter) obstacle designs (405) are fed as training data to a Geometric FNO model (410). Simulations on the designs provide bacteria density profiles (415) indicative of how well each design prevents upstream mobility. These profiles create a design space (420) wherein an optimum obstacle design can be determined (425).

Figure 5A:
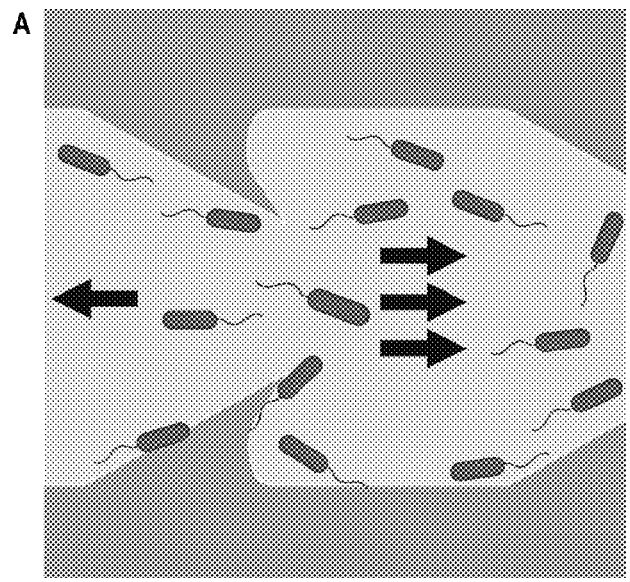
FIGS. 5A-5F show examples of the physical mechanism of using obstacles in channel geometries to impede upstream mobility.
Figure 5B:
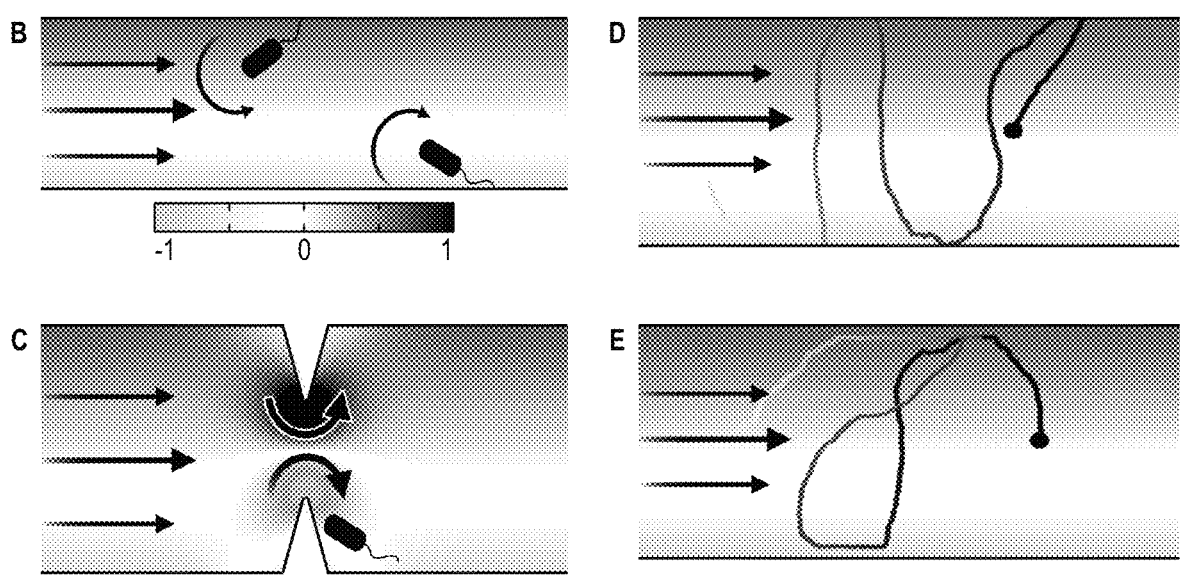
Figure 5C:
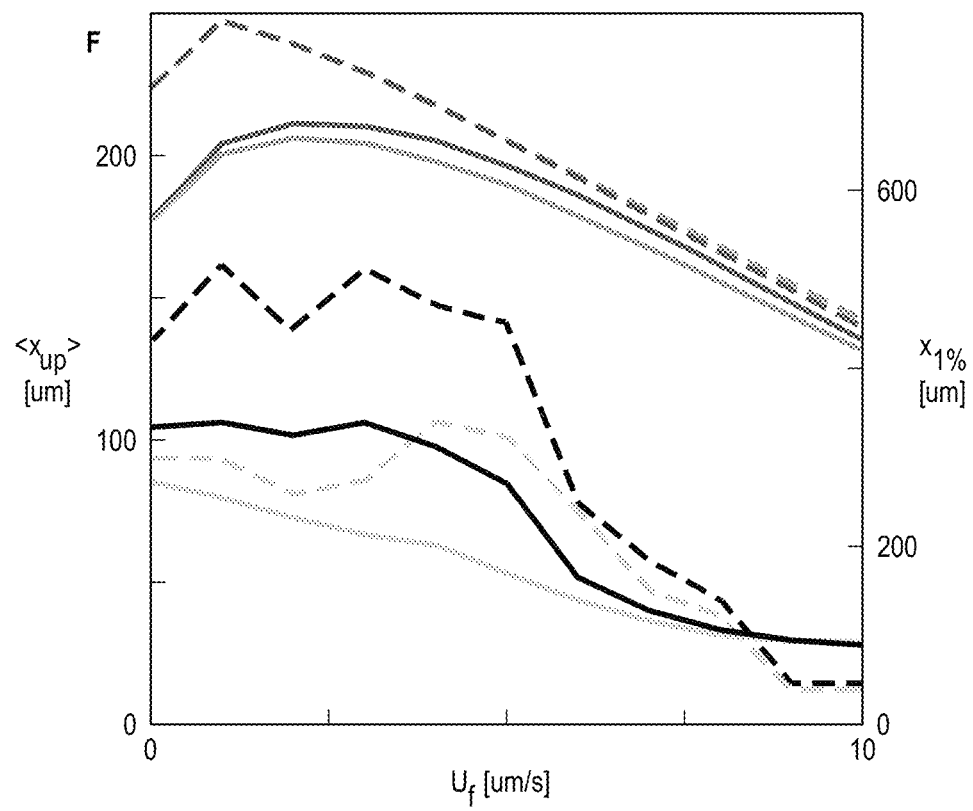
Figure 5D:
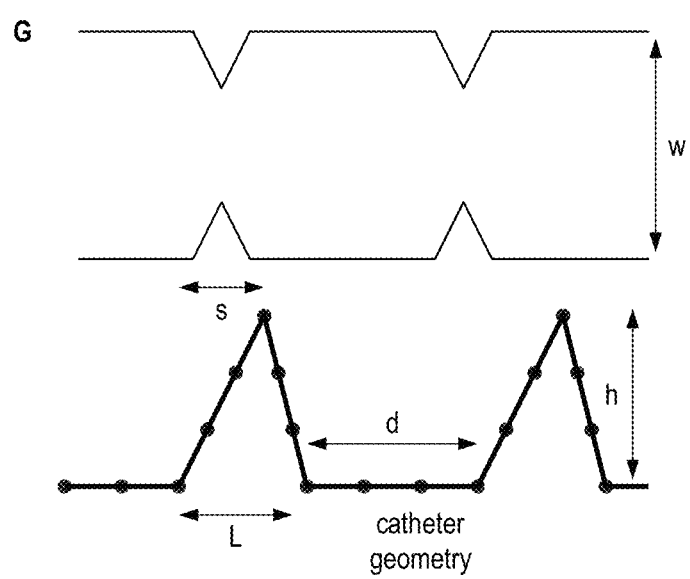
Figure 5E:
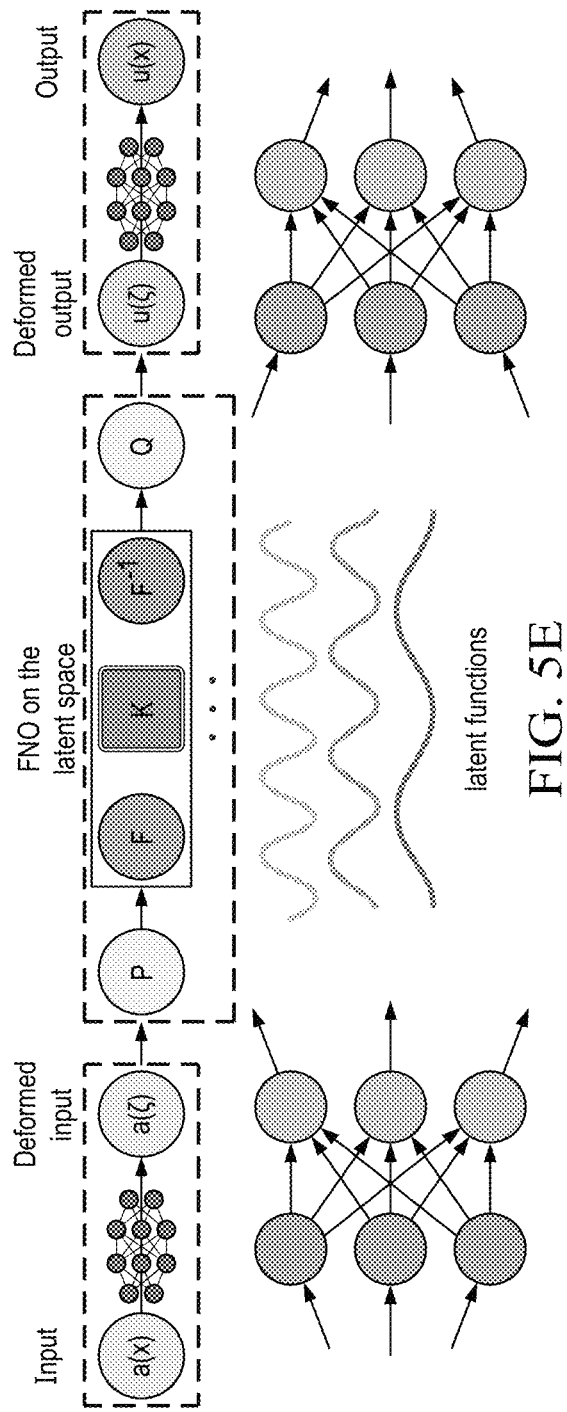
Figure 5F:
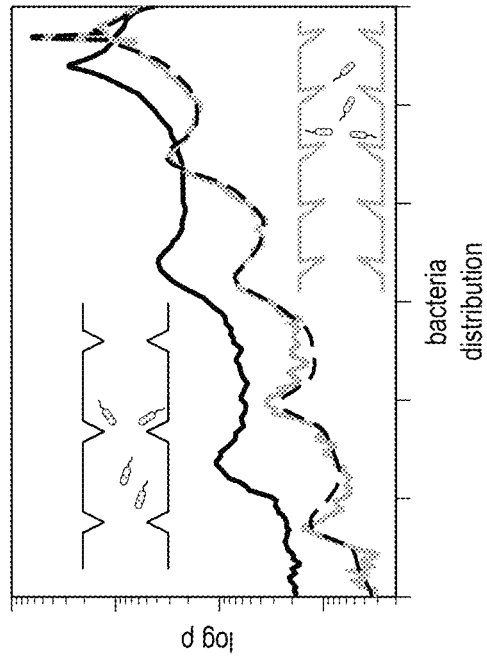

FIGS. 5A to 5E shows an example of the physical mechanism of obstacles suppressing upstream mobility with geometric optimization. FIG. 5A shoes the geometric rectification without flow. FIG. 5B shoes flow voracity due to obstacles in the channel, with Poiseuille flow without obstacles and enhanced voracity with obstacles. FIG. 5C shows examples of bacteria population statistics due to upstream mobility. FIG. 5D shows the channel geometry parameters used for the modeling. FIG. 5E shows an example of the AI-model. The Geo-FNO model is designed to learn the relationship between catheter geometry and bacteria distribution. It accomplishes this through a series of neural operator layers. The Geo-FNO first maps the irregular channel geometry to a unit segment [0,1], then applies Fourier-based kernels in the latent space, and finally transforms the predicted bacteria distribution in the latent space back to the physical space. The bacteria distribution corresponding to the optimized design predicted by Geo-FNO can be verified by the fluid and particle dynamics simulation, as shown in FIG. 5F.

Figure 6A:
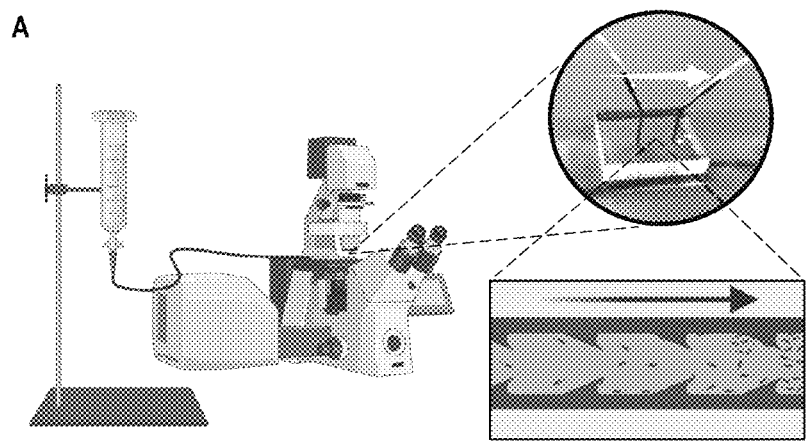
FIGS. 6A-6E show examples of microfluidic experiment results.
Figure 6B:
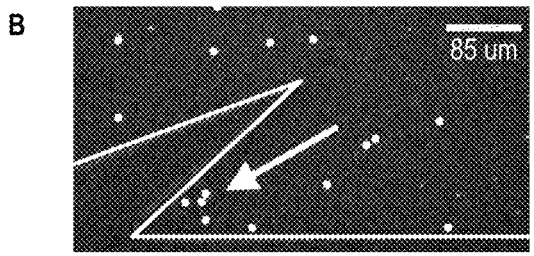
Figure 6C:
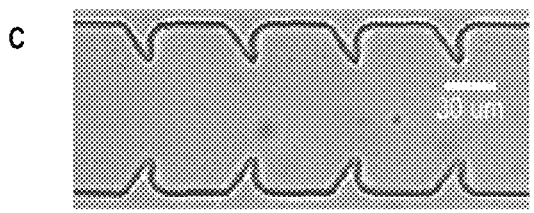
Figure 6D:
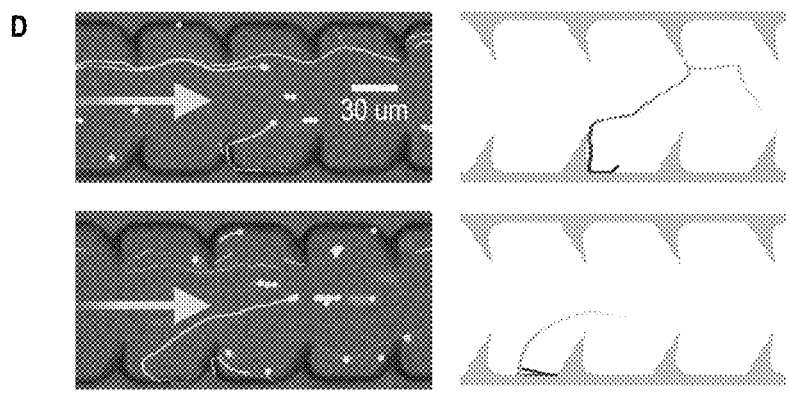
Figure 6E:
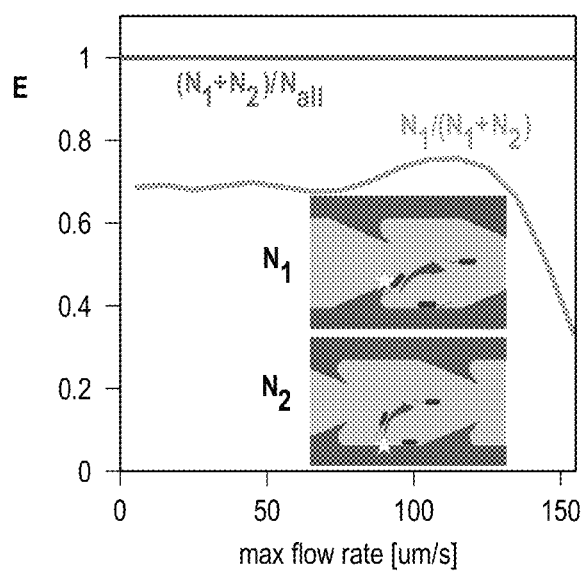

FIGS. 6A to 6E show an example of Microfluidic experiments. FIG. 6A shows an example schematic of microfluidic experiments. One end of the microfluidic channel is connected to a syringe filled with imaging solution, while the other end is connected to a reservoir of bacteria. The long arrow denotes the flow direction. FIG. 6B shows bacteria accumulation at the sharp corner of the obstacle due to flow stagnation. FIG. 6C shows a bright field image of the microfluidic channel. FIG. 6D shows typical events of bacteria (white dots) falling off the channel walls, with their trajectories of the past 5 seconds shown in lines trailing the bacteria. The upper image shows a "type 1" trajectory where the bacteria fall off from the obstacle tip. The lower image shows a typical "type 2" trajectory where the bacteria fall off from the smooth part of the wall. Left column experimental, right column simulation. FIG. 6E shows example statistics of fall-off events.

FIGS. 7A and 7B show example graphs of results for experiments done with 3D-printed catheter prototypes. FIG. 7A shows bar graphs for bacterial contamination in a smooth (no obstacles) channel for regions 1-6 (1 being furthest upstream and 6 being furthest downstream) shown left to right in the graphs. FIG. 7B shows a comparison of the first three regions (furthest upstream) in smooth vs. designed channels. The graph shows a marked improvement in the use of the obstacles in preventing upstream mobility.

FIGS. 8A to 8D show example cross-sections of a channel wall with improved obstacles (not drawn to scale) and the parameters that could be used in the optimization process (or in describing the obstacles).

Figure 8A:
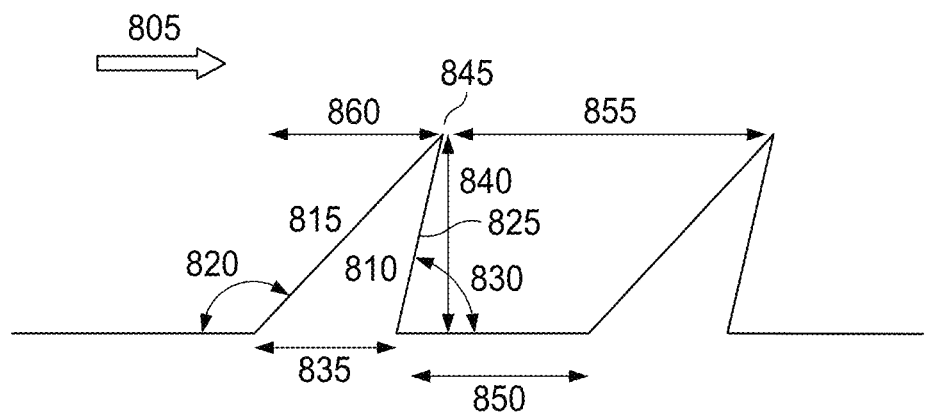
FIGS. 8A-8D show examples of channel geometry cross-sections.

FIG. 8A shows an example triangular obstacle. In a channel with a flow direction (805), the obstacles (810) can be parameterized as having, for example, a side (815) facing towards the flow direction (i.e., towards the upstream end of the channel) with an obtuse angle (greater than 90 degrees) (820), a side (825) away from the flow direction (i.e., towards the downstream end of the channel) with an acute angle (less than 90 degrees) (830), a base width (835) (also known as parameter "L" herein; see FIG. 5D), a height (840) from the wall (or base) to the vertex (845) of the obstacle (also known as parameter "h" herein; see FIG. 5D), a base inter-obstacle distance (850) from base to base (also known as parameter "d" herein; see FIG. 5D), a vertex inter-obstacle distance (855) from vertex to vertex, and/or an x-component (parallel to the wall) distance (860) from the upstream end of the base to the vertex (also known as parameter "s" herein; see FIG. 5D).

Figure 8B:
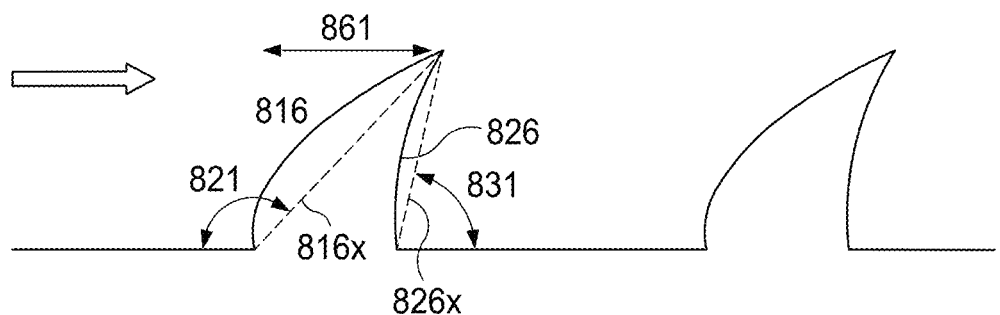

FIG. 8B shows an example triangular obstacle with curved sides (816, 826). The parameters are largely the same as the non-curved triangle (FIG. 8A), but the angles (821, 831) are measured against planes (816x, 826x) from the upstream/downstream side of the base to the vertex (i.e., as if the side was not curved). The "s" parameter (861) is still measured from the upstream end of the base to the vertex. In some embodiments, the curvature of the sides can be parameters. In some embodiments, both sides are curved. In some embodiments, only one side is curved.

Figure 8C:
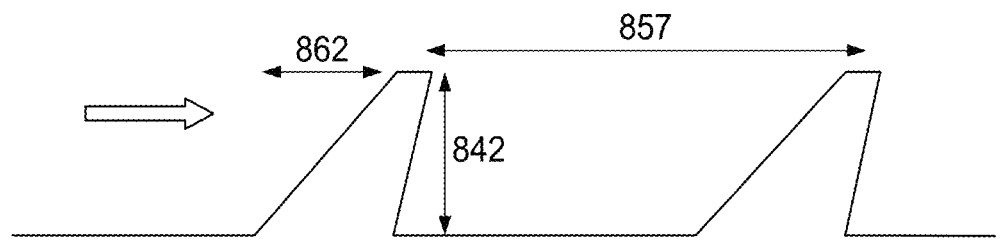

FIG. 8C shows an example trapezoidal obstacle (or, a triangular obstacle with the vertex sheered away). Again, the parameters are largely the same as the triangular obstacle (FIG. 8A), but the "s" parameter (862) is measured from the upstream end of the base to the upstream end of the top. The height (842) is measured from the wall to the highest part of the obstacle. The "vertex" inter-obstacle distance (857) is measured from corresponding same points of the tops of the obstacles (in this example, from center to center). In some examples the obstacles also have one or more curved sides, as shown in FIG. 8B.

Figure 8D:
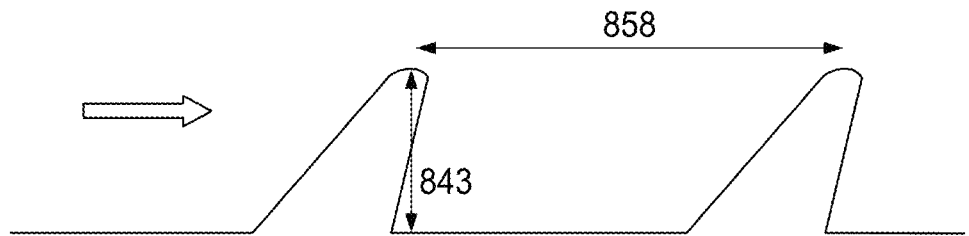

FIG. 8D shows an example triangular obstacle with a rounded vertex. Again, the parameters are largely the same as the triangular obstacle (FIG. 8A), but the height (843) is measured from the wall to the highest part of the obstacle. The "vertex" inter-obstacle distance (858) is measured from corresponding same points of the tops of the obstacles (in this example, from center to center). In some examples the obstacles also have one or more curved sides, as shown in FIG. 8B.

Figure 9:
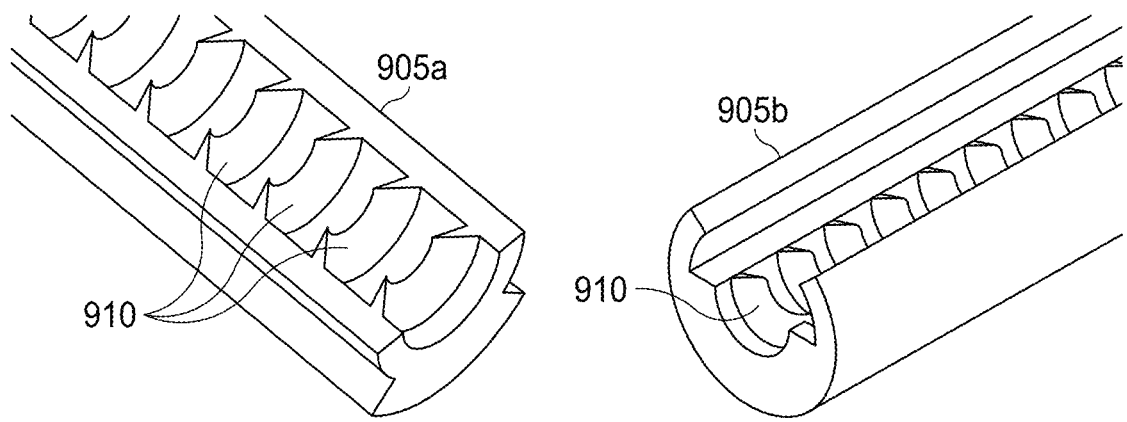
FIG. 9 shows an example of a plan view of a two-part flow channel with obstacles.

FIG. 9 shows an example catheter design assembled from two halves (905a, 905b) and joined together in a mortise and tenon structure. The inside of the tube has periodic flappers (obstacles) (910) similar to a bamboo structure. In some embodiments the obstacles are contiguous around the inner diameter of the channel. In some embodiments the obstacles are non-contiguous around the inner diameter.

Figure 10:
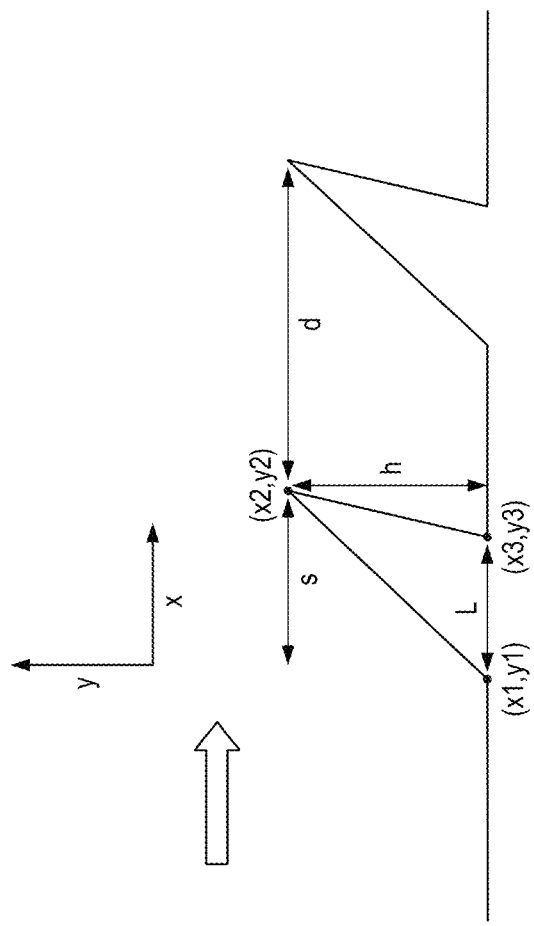
FIG. 10 shows an example of obstacle design based on a coordinate system.

FIG. 10 shows an example representation of the obstacles using x,y coordinate oriented parameters. With this, three key points on the obstacle are designated (x1,y1), (x2,y2), and (x3,y3). If (x1,y1) is set to (0,0), then the corresponding parameters would be x2=s, y2=h, x3=L, and y3=0, giving the three coordinates as (0,0), (s,h), and (L,0).

As shown in FIGS. 11D-11E and 12C-12F, these parameters can fall into preferable ranges where loss (e.g., FIG. 12F) is minimized.

In some embodiments, these ranges of these parameters for a channel of width (W) 10 μm<W<1 cm and length M are:

| d | s (x2) | h (y2) | L (x3) |
|---|---|---|---|
| 20 μm < d < M | X3 < x2 < d/2 | 5 μm < y2 < W/2 | 2 μm < x3 < x2 |

In some embodiments, these ranges of these parameters for a tubular channel (e.g., catheter) of inner diameter (D) of 1 mm<D<5 mm and length M are:

| d | s (x2) | h (y2) | L (x3) |
|---|---|---|---|
| 20 μm < d < M | X3 < x2 < d/2 | 5 μm < y2 < D/2 | 2 μm < x3 < x2 |

In some embodiments, the tubular channel has an inner diameter (D) of 1.5 mm to 2.5 mm and a distance between obstacles (d) of 0.3 to 0.6 mm, and the coordinate values are point 1 (x1,y1)=(0,0); point 2 (x2, y2): (x3<x2<x3+0.5 mm, 0.3 mm<y2<0.5 mm); and point 3 (x3, y3): (0.08 mm<x3<d/4).

For catheters for larger or smaller animals with different sized ureters, the preferred parameter range is the same but rescaled according to the corresponding ureter size.

In terms of manufacturing methods, any methods that work well in this range of parameters are suitable, including but not limited to 3D printing, injection molding, extrusion molding, CNC (computer numerical control) machining, polymer casting and thermoforming.

The fluidic channel can be made of any standard material, including but not limited to silicone rubber, nylon, polyurethane, polyethylene terephthalate (PET), latex, Teflon™ and combinations thereof.

Figure 11A:
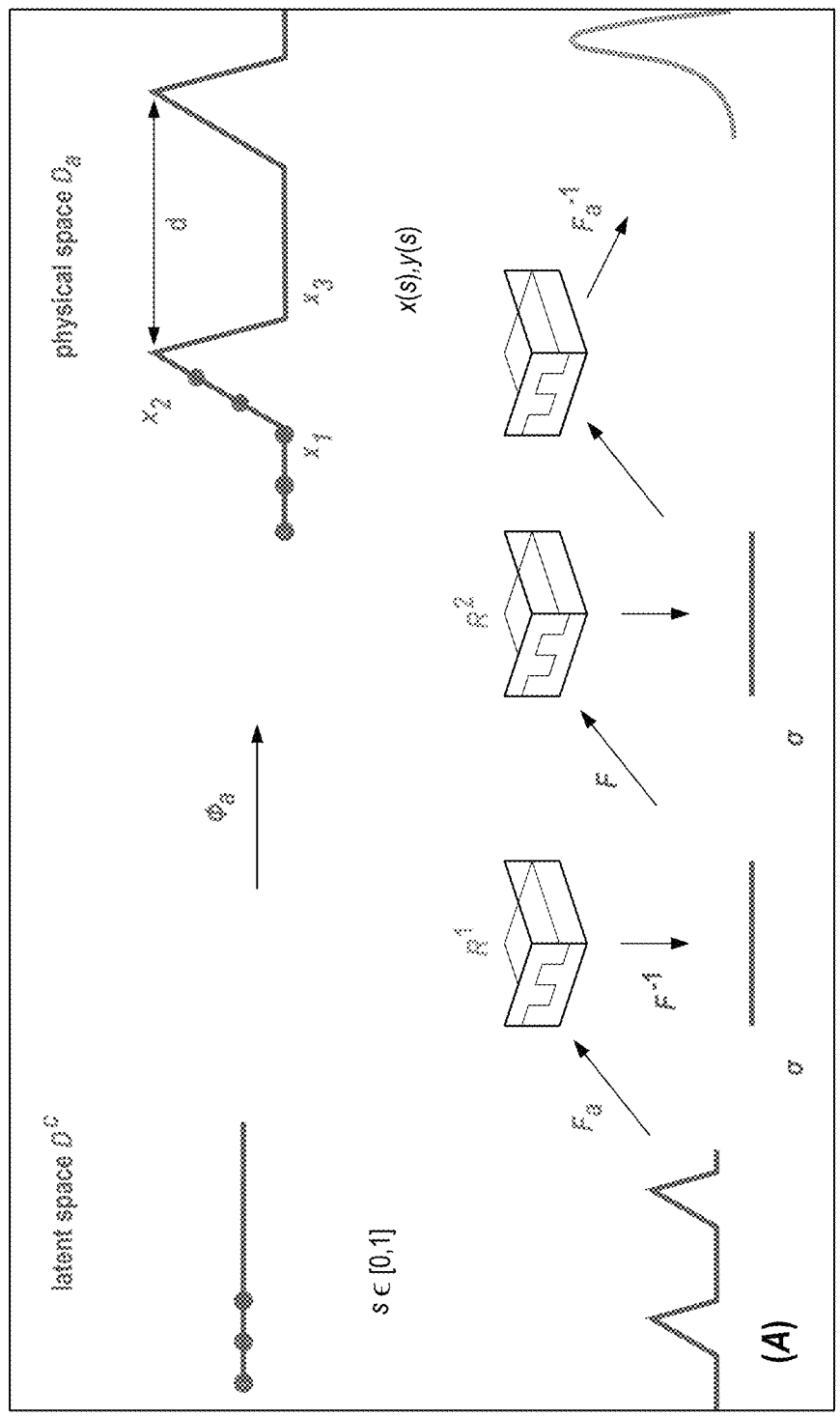
FIGS. 11A-11E show an example of optimizing design using coupled fluid and particle dynamics simulation and Geo-FNO machine learning method.

FIGS. 11A-11∈show an example of optimizing geometry design using coupled fluid and particle dynamics simulation and Geo-FNO machine learning method. FIG. 11A shows a schematic of Geometry-Aware Fourier Neural Operator. FIG. 11B shows training and test loss evolution. Inset compares the Geo-FNO prediction and particle simulation results for a typical design. FIG. 11C shows optimized triangle-shaped design and simulation validation. FIGS. 11D and 11∈show the loss landscape from Geo-FNO predictions at two selected cross sections of the parameter space.

Optimization of Geometric Conditions for Suppressing Upstream Swimming

With the physical insight from the numerical simulations, the Geo-FNO framework can be used in some embodiments to accelerate optimization of the obstacle shape. Particle simulations can be performed using both the ABP and Levy RTP models for multiple flow rates (e.g., 5, 10, 15 um/s) as training data for the FNO. The design in each simulation is randomly selected from a parameter space: e.g., channel width W=100 um, triangles of height 20 um<h<30 um are periodically placed on the channel walls with periodicity 60 um<d<250 μm, and the base length of these triangles are 15 um<x3−x2<d/4. The left vertex is located at x1=−d/2. The relative horizontal position of the upper vertex is −d/4<x2−x1<d/4 (See FIG. 10). To evaluate the efficiency of each design parameter combination, adopt the loss function, Loss( ), that emphasizes on the bacteria going farthest upstream:

$$\text{minimize Loss}(\theta) = -\int_0^\infty \rho(x;\theta)x\,dx$$

Where $\rho(x; \theta)$ is the averaged population of the bacteria at time T for these three flow rates, with $-x$ the upstream direction, and $\theta$ the combination of the geometric parameters (d, h, x2, x3).

Figure 11B:
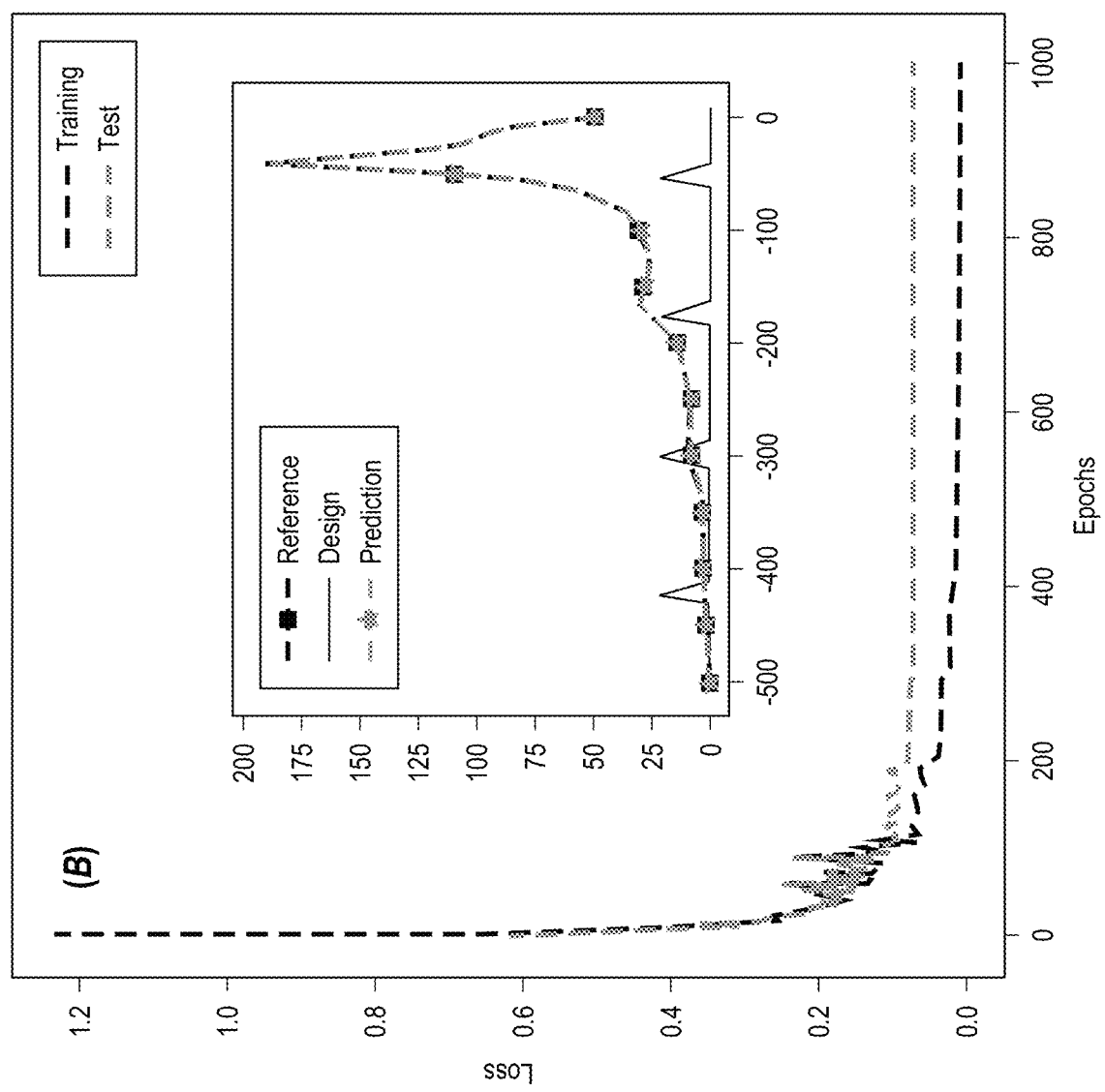

As shown in FIG. 11A, the deformation map $\Phi_a$ maps the latent space [0,1] to the shape of the catheter tube (e.g. of length 500 µm), which is represented by the curve $\{(x(s), y(s)):s\in[0,1]\}$ with normalized arc length s. Geo-FNO maps the curve to the bacterial population $\rho(x; \theta)$ at T=500 secs through the geometric Fourier transforms $F_a$, $F_a^{-1}$ and 5 Fourier layers with the GeLU activation function parameterized by $R_i$, following. In an example, generate 1000 training data and 100 test data and use relative empirical mean square error as the loss function. FIG. 11B shows both training and test errors converge without overfitting, and one randomly picked test result is also presented. The test error is about 0.07. After training is done, a randomized BFGS (Broyden-Fletcher-Goldfarb-Shanno) method is used to search for the optimal $\theta$ corresponding to a minimal value of d.

These constraints are enforced with sigmoid transformation functions. Initialize the design with $\theta=81$, which corresponds to $d=6.68\times10^5$. The final design is $\theta=(62.26, 30.0, -11.57, -15.86)$ and $d=2.18\times10^5$.

Figure 11C:
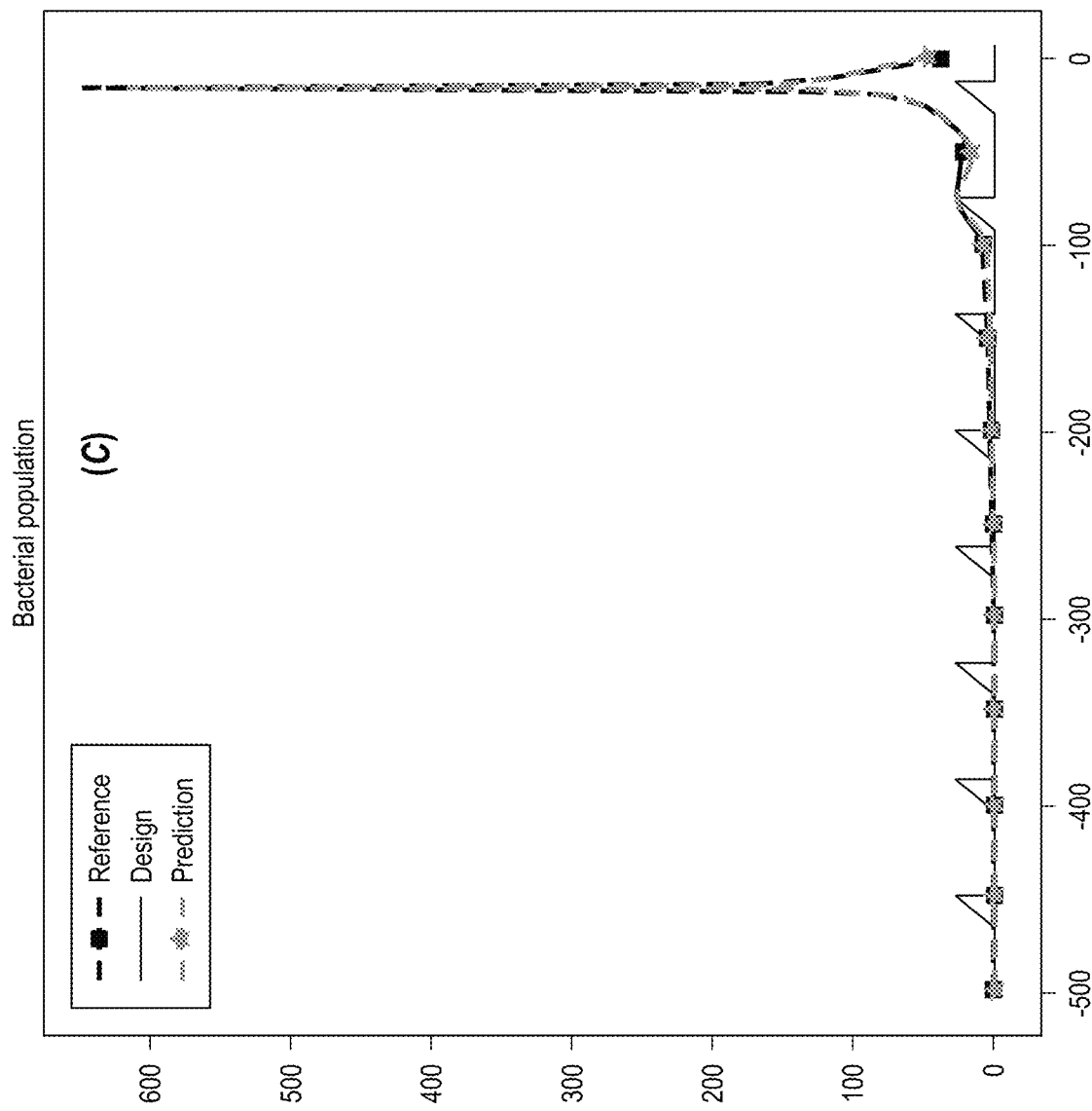

The verification of the final design with the ABP and Levy RTP models is depicted in FIG. 11C.

Figure 11D:
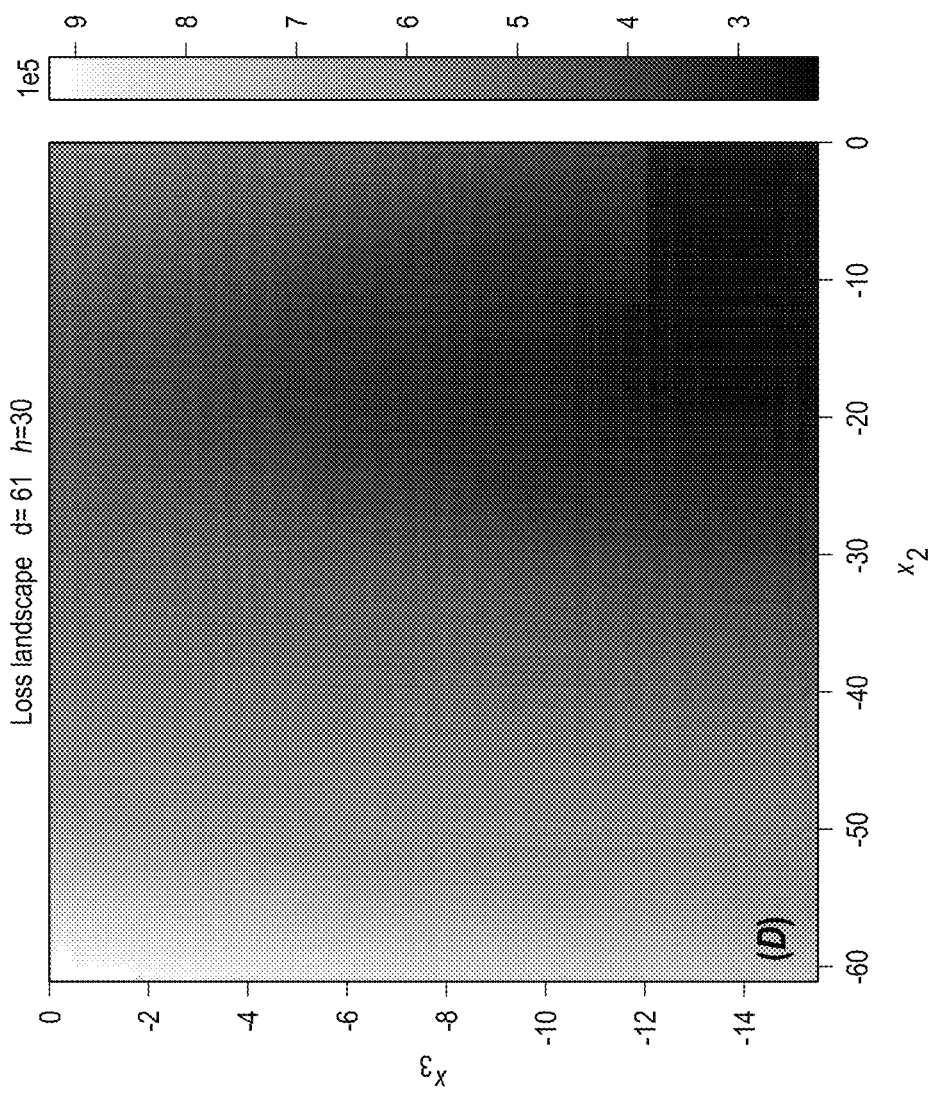
Figure 11E:
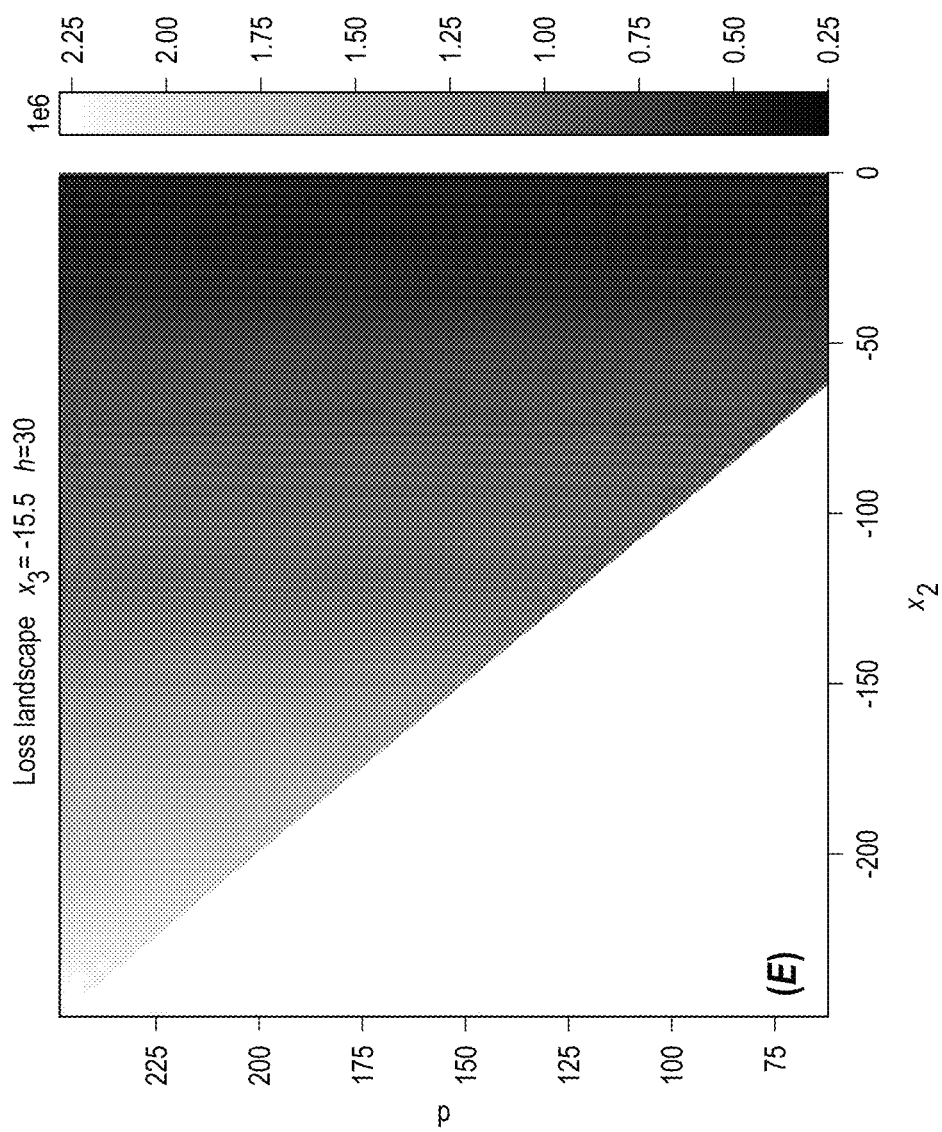

Good agreement is achieved. As shown in FIG. 11D and FIG. 11E, within fabrication limits, the loss decreases with smaller inter-obstacle distance d. Interestingly, given optimal d and h, the loss landscape is non-monotonic with respect to the x2 value. Based on these optimization results, one can choose to fabricate the optimal shape.

Figure 12A:
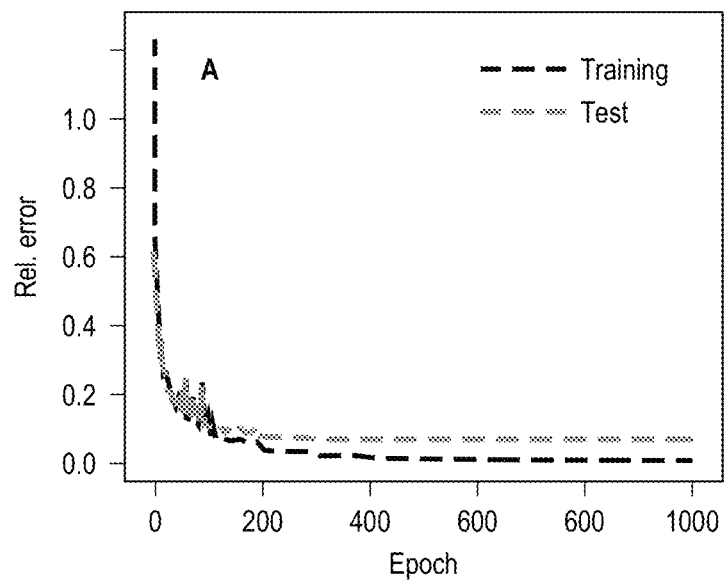
FIGS. 12A-12F show an example of optimization visualization.
Figure 12B:
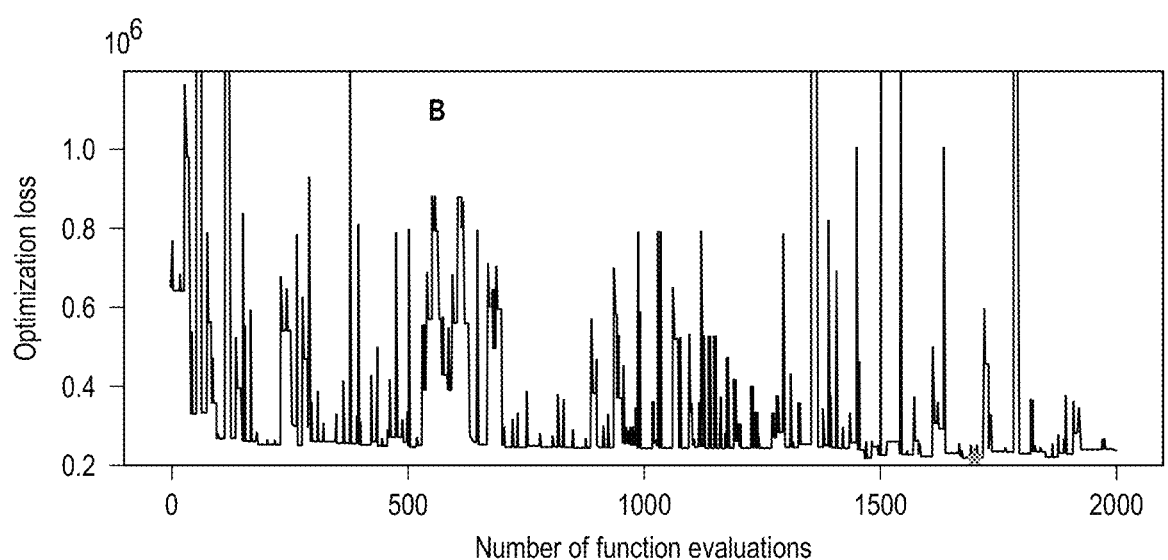
Figure 12C:
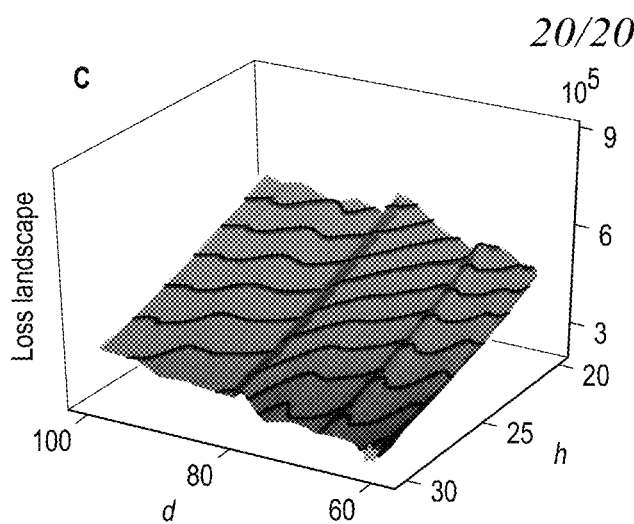
Figure 12D:
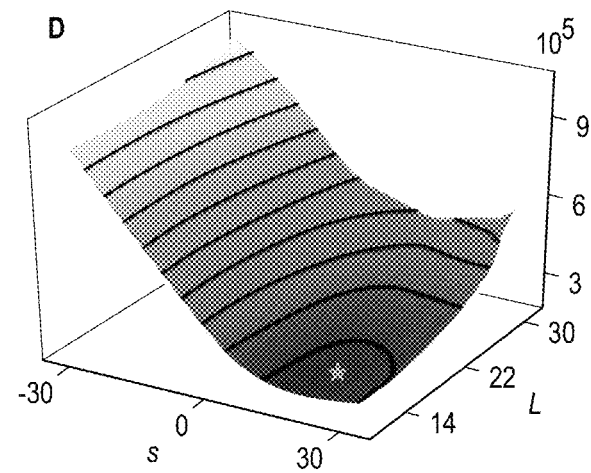
Figure 12E:
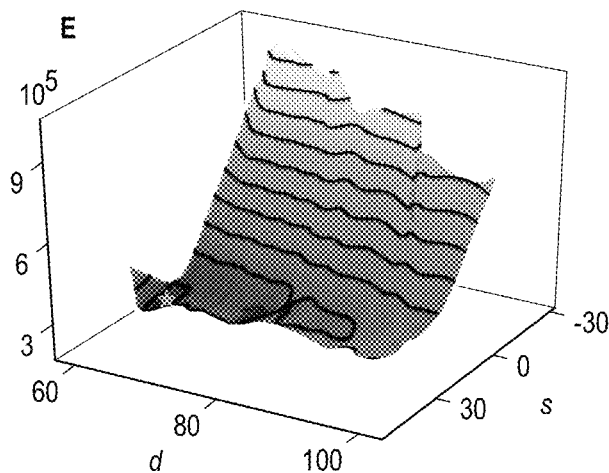
Figure 12F:
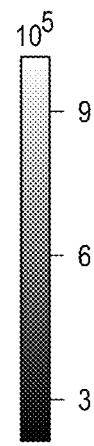

FIGS. 12A-12F shown an example of optimization visualization. FIG. 12A shows training and test errors for Geo-FNO, both errors converge without overfitting; FIG. 12B shows optimization loss obtained by the randomized BFGS algorithm accelerated by a Geo-FNO surrogate model, the recorded-global loss is obtained at about 1500 iterations. FIG. 12C shows visualization of the loss landscape around the optimized design at the d–h cross-section obtained by Geo-FNO; FIG. 12D shows visualization of the loss landscape around the optimized design at the s–L cross section obtained by Geo-FNO; and FIG. 12E shows visualization of the loss landscape around the optimized design at the d-s cross-section obtained by Geo-FNO. FIG. 12F shows the gradient scale key of "loss" for FIGS. 12C-12E.

Training the Geo-FNO model on 1000 simulations uniformly generated from the design space, and testing it on 100 randomly generated designs resulted in FIGS. 12A-12F. The model takes the shape of the channel as the input, and outputs the bacteria density as a 1 D function. The training error and test error are depicted in FIG. 12A, no overfitting is observed, and the average relative test error is about 4%. After training, each evaluation of the map from the channel geometry to the bacterial population takes only 0.005 seconds on GPUs in contrast to 10 minutes by using coupled fluid-particle simulations, and therefore it is affordable to do thousands of evaluations in the optimization procedure.

For an example of the optimization, the forward map takes these four design parameters d, L, h, s, generates channel geometry, predicts the bacteria population with Geo-FNO, and finally computes the objective function $<x_{up}>$. Automatic differentiation tools embedded in the deep learning package (i.e., Pytorch) are used to efficiently compute gradients with respect to design variables enabling the use of gradient-based design optimization methods. Start from initial design parameters (d=100, h=25, s=10, L=20) µm, and update them using the BFGS algorithm with Strong Wolfe line search to minimize the objective function $<x_{up}>$. To enforce the constraints about these design parameters, exponential transforms are applied to the design parameters. For example, to enforce $x_{min}\leq x\leq x_{max}$, x is defined as $x=\varphi(\theta)=x_{min}+(x_{max}-x_{min})/(1+e^\theta)$. This ensures that Geo-FNO remains in the interpolation regime and the final design satisfies manufacturing conditions. Another challenge is related to local minimizers, since most partial differential constraint optimization is non-convex. When the optimization gets trapped in a local minimizer, the optimization restarts from an initial condition obtained by perturbing the recorded-global minimizer with a random Gaussian noise sampled from N (0,I). The optimization loss vs. Optimization iteration curve is depicted in FIG. 12B. The recorded global minimizer is obtained at about 1500 iterations, the loss is reduced from $<x_{up}>=6.68\times10^5$ to $<x_{up}>=2.18\times10^5$. Several cross-sections of the loss function landscape around the final optimized design are presented in FIG. 12C-F. The Geo-FNO model is more interpretable as opposed to a black box model that directly outputs design parameters for shapes of the triangles in the catheter, without estimating the full flow field. Further, Geo-FNO is more accurate than the simpler black box model (a standard multi-layer perceptron or MLP) that directly predicts the design parameters. With the same amount of training dataset, Geo-FNO gets a 2.5% error on averaged bacteria density, while MLP gets a 3.1% error.

Within imposed parameter constraints, the landscape near the optimized design is neither convex nor monotonic with respect to these design variables, but the loss is generally smaller with larger h, larger s, smaller d, which indicates the channel design is more effective when the height of the obstacle is large, the tip points towards downstream, and obstacles are more frequent.

Example Experimental Setup

Wild-type BW25113 E. coli with kanamycin resistance for the 3D catheter long-term experiment and BW25113 E. coli expressing mScarlet red fluorescent protein with kanamycin resistance were used for microfluidic experiments. A single colony of the bacterium of interest was picked from a freshly streaked plate and suspended in LB medium to create a bacterial inoculum. The starting culture was cultured overnight at 37° C. in LB medium to achieve a final concentration of approximately OD600 0.4. For the microfluidic experiments, 300 µL of the starting culture is transferred to a new flask with 100 mL LB median and cultured at 16° C. until OD600 reaches 0.1-0.2. Bacteria are washed twice by centrifugation (2300 g for 15 min), and the cells were suspended in a motility imaging medium composed of 10 mM potassium phosphate (pH 7.0), 0.1 mM K-EDTA, 34 mM K-acetate, 20 mM sodium lactate, and 0.005% polyvinylpyrrolidone (PVP-40). The use of this medium allows for the preservation of bacterial motility while inhibiting cellular division. The final concentration of the bacteria in the reservoir has OD600 at 0.02. For the 3D catheter long-term experiments, 3 mL of the starter culture is transferred to a new flask with 500 mL LB median and cultured at 16° C. until OD600 reaches 0.4. The bacteria are directly used and injected into the bacteria reservoir. Kanamycin was added to all the culture median and LB plates. The mobility of the bacteria was checked under the fluoresce microscope 10 min before the experiment (observed under DIC for BW25113 and RFP for the BW25113 mScarlet strain).

To demonstrate the mechanism of the design and test the effectiveness of the optimized structure, quasi-2D microfluidic channels were fabricated to observe bacteria motion under a microscope. These microfluidic devices were fabricated using photolithography and PDMS soft-lithography. As shown in the schematic of FIG. 6A, one end of the microfluidic channel connects to a syringe filled with imaging solution, and the other end connects to a reservoir of E. coli. The flow rate is controlled by tuning the height of the syringe with respect to the outlet downstream. Fluorescent beads were injected into the imaging solution as passive tracers to monitor the flow rate in real time. The high-speed video was achieved using an Olympus BX51WI microscope with two Photometrics Prime95B cameras connected using a W-View Gemini-2 Optical Splitter from Hamamatsu. An Olympus 20× dry objective lens was used. Time-lapse images were acquired at 12.4 frames per second with 488 nm laser intensity set at 20%. The microscope's focal plane was fixed near the middle of the channel in the depth z-direction to avoid recording bacteria crawling on the top and bottom sides of the channel. Experiments were performed on three different days with independent batches of E. coli. cultures, with five 15-minute recordings each day. ImageJ software (Fiji) was used for video post-processing to extract the trajectories of the bacteria. The trajectories are filtered by their linearity of forward progression to eliminate the fast-moving downstream ones and visually highlight the upstream swimming ones. The time interval for the upstream swimming is estimated to be 10 s before the fall-off. The maximum flow speed is defined as the highest flow speed along the channel's centerline. The instantaneous maximum flow rate is estimated by averaging the fastest velocities of bacteria and fluorescent beads along the centerline during the upstream-fall-off interval. Several video recordings are provided in the supplementary materials.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The following are claimed:

1. A method of making a catheter having a urine flow direction, the method comprising:
    providing a catheter tube with an inner channel;
    providing a plurality of protuberances on an interior surface of the inner channel, each of the protuberances having a first side facing into the flow direction at a first angle from the interior surface and a second side facing away from the flow direction at a second angle from the interior surface and a vertex between the first side and the second side and a base length from where the first side connects to the interior surface to where the second side connects to the interior surface, each of the plurality of protuberances being configured to create vortices during a flow of fluid in the urine flow direction;
    the first angle being different from the second angle, such that each protuberance has an asymmetrical profile and wherein the first angle is greater than 90 degrees and the second angle is less than 90 degrees; and
    the base length of each of the plurality of protuberances being less than one half the distance between vertices of adjacent protuberances;
    wherein the providing the plurality of protuberances comprises optimizing geometry parameters of the plurality of protuberances by a geometric Fourier neural operator model.

2. The method of claim 1, wherein the catheter has an outer diameter from 5 to 36 Fr.

3. The method of claim 1, wherein catheter has a channel width from 1 to 100 mm.

4. The method of claim 3, wherein each of the plurality of protuberances has a height equal to or less than 30% of the channel width.

5. The method of claim 1, wherein the providing the plurality of protuberances comprises one or more of: 3D printing, injection molding, extrusion molding, computer numerical control machining, polymer casting, and thermoforming.

6. The method of claim 1, wherein the plurality of protuberances is composed of silicone rubber, nylon, polyurethane, polyethylene terephthalate, latex, polytetrafluoroethylene, or combinations thereof.

7. The method of claim 1, wherein the geometric Fourier neural operator model is trained as a surrogate model for a forward fluid and particle dynamics simulation that maps the geometry parameters to a bacteria population function.

* * * * *